(12) United States Patent
Wada et al.

(10) Patent No.: US 9,358,335 B2
(45) Date of Patent: Jun. 7, 2016

(54) PUNCTURE DEVICE

(75) Inventors: Satoshi Wada, Shizuoka (JP); Katsuaki Soma, Shizuoka (JP); Hiroshi Yagi, Shizuoka (JP)

(73) Assignee: TERUMO KABUSHIKI KAISHA, Shibuya-Ku, Tokyo (JP)

( * ) Notice: Subject to any disclaimer, the term of this patent is extended or adjusted under 35 U.S.C. 154(b) by 1200 days.

(21) Appl. No.: 11/885,046

(22) PCT Filed: Feb. 16, 2006

(86) PCT No.: PCT/JP2006/302762
§ 371 (c)(1),
(2), (4) Date: Jul. 28, 2008

(87) PCT Pub. No.: WO2006/090637
PCT Pub. Date: Aug. 31, 2006

(65) Prior Publication Data
US 2009/0105651 A1    Apr. 23, 2009

(30) Foreign Application Priority Data

Feb. 25, 2005 (JP) ................. 2005-050862

(51) Int. Cl.
A61M 5/178 (2006.01)
A61M 5/158 (2006.01)
A61M 25/06 (2006.01)

(52) U.S. Cl.
CPC ............ *A61M 5/158* (2013.01); *A61M 25/06* (2013.01); *A61M 25/0693* (2013.01); *A61M 2025/0687* (2013.01)

(58) Field of Classification Search
USPC ........................ 604/164.01, 164.06, 164.09
See application file for complete search history.

(56) References Cited

U.S. PATENT DOCUMENTS

| | | | |
|---|---|---|---|
| 3,540,447 A | 11/1970 | Howe | |
| 4,781,691 A * | 11/1988 | Gross | 604/164.06 |
| 5,893,844 A * | 4/1999 | Misawa | 604/195 |
| 6,203,533 B1 * | 3/2001 | Ouchi | 604/264 |
| 6,440,119 B1 | 8/2002 | Nakada et al. | |

FOREIGN PATENT DOCUMENTS

JP  50-158194  12/1975
JP  4-58257 U  5/1992
(Continued)

*Primary Examiner* — Edelmira Bosques
(74) *Attorney, Agent, or Firm* — Buchanan Ingersoll & Rooney PC

(57) ABSTRACT

A puncture device is provided that does not allow an outer needle to collapse or rise at the time of puncture and exhibits small puncture resistance.

A puncture device 1 includes: a hollow outer needle 2; an outer needle hub 3 provided at a proximal end portion of the outer needle 2; a hollow inner needle 4 inserted into the outer needle 2 for use; and an inner needle hub 5 provided at a proximal end portion of the inner needle 4. The inner needle 4 includes, from the distal side, a sharp needlepoint 41, a small diameter portion 42 having an almost uniform outer diameter; an intermediate portion 43 formed as a tapered portion which is progressively increased in outer diameter as it goes toward the proximal end; and a larger diameter portion 44 having inner and outer diameters larger than inner and outer diameters, respectively, of the small diameter portion 42. If the puncture device 1 is assembled, the needlepoint 41 is most projected from the distal opening 24 of the outer needle 2 and the proximal end of the small diameter portion 42 and the distal end of the large diameter portion 4 are located inside the outer needle 2. The inner diameter of the outer needle 2 at a portion L1 where the outer needle 2 covers the small diameter portion 42 of the inner needle 4 is smaller than the large diameter portion 44 of the inner needle 4.

28 Claims, 3 Drawing Sheets

(56) References Cited

FOREIGN PATENT DOCUMENTS

| JP | 3026200 U | 7/1996 |
|---|---|---|
| JP | 11-89939 A | 4/1999 |
| JP | 2001-112871 A | 4/2001 |
| JP | 2002-058747 A | 2/2002 |
| JP | 2004-41492 A | 2/2004 |
| JP | 2005-230308 A | 9/2005 |
| WO | WO 94/11042 | 5/1994 |

* cited by examiner

PUNCTURE DEVICE

TECHNICAL FIELD

The present invention relates to a puncture device.

BACKGROUND ART

A treatment of inserting a catheter such as a balloon catheter and a guiding catheter or a lead wire of a cardiac pacemaker into a blood vessel is performed by using an indwelling needle assembly (see e.g. Patent Document 1) and a sheath introducer. The indwelling needle assembly includes an outer needle and an inner needle inserted into the outer needle. The sheath introducer includes a sheath and a dilator inserted into the sheath.

In general, an indwelling needle assembly in which an outer needle and an inner needle are assembled together (a needlepoint of the inner needle projects from the tip of the outer needle) is inserted into a blood vessel such as a femoral artery. The inner needle is next withdrawn from the outer needle to indwell only the outer needle. A guide wire is inserted into the inside of the blood vessel through the outer needle. A sheath introducer in which a sheath and a dilator are assembled together is inserted onto the guide wire, introduced into the blood vessel and advanced to a desired position. Thereafter, the dilator and the guide wire are withdrawn to indwell the sheath in position. Thus, the inside of the blood vessel can directly be accessed from outside of the body of a patient through the sheath. This makes it possible to introduce catheters of various types or the lead wire of the cardiac pacemaker into the blood vessel via a sheath.

The indwelling needle assembly (puncture device) mentioned above is needed to give small damage to a blood vessel at the time of puncture and to easily catch the blood vessel. It is thus preferred that the inner needle and the outer needle are as thin as possible (have respective small outer diameters).

However, if a needle tube is made thin, its strength is reduced to become yielding, deteriorating puncture performance (accessibility of a needlepoint to a target site of a living body). In other words, the resistance of skin, subcutaneous fat, muscle tissue or the like deforms the needle tube, which makes it impossible for the needlepoint to reach a targeted blood vessel. In particular, if a puncture is made to an artery located deep in the living body, such a defect appears dominantly and high frequently.

The needlepoint of the inner needle which has caught the blood vessel can be confirmed by visually observing the inflow (flashback) of blood into an inner hub provided at the proximal end of the inner needle. If the inner needle is made thin to reduce its inner diameter, a time difference increases between an actual puncture of the needlepoint into the blood vessel and the confirmation of the flashback. This may make it probable not to accurately and quickly recognize catch of the blood vessel.

At the time of confirming the flashback, usually the inner needle and outer needle are slightly advanced (based on a sense or experience of an operator, the inner and outer needles are slightly advanced in a delicate distance). This determines that the tip of the outer needle has been inserted into the inside of the blood vessel. However, the late flashback has a bad influence on the operation of advancing the inner and outer needles in a delicate distance. For instance, the inner needle may be inserted too deep so that it injures the opposite side of the blood vessel or impales the blood vessel.

To quickly recognize the flashback, a puncture device 100 including an inner needle 104 with the so-called different diameters as shown in FIG. 6 has been devised as below. The inner needle 104 includes a small diameter portion 142, a large diameter portion 144 and a tapered intermediate portion 143. The small diameter portion 142 is located on the proximal end side of the needlepoint 141. The large diameter portion 144 is located closer to the proximal end than the small diameter portion 142 and has inner and outer diameters greater than those of the small diameter portion 142. The intermediate portion 143 is located between the small diameter portion 142 and the large diameter portion 144 so as to be formed to alleviate the changes in the inner and outer diameters of the small and lager diameter portions 142, 144.

The puncture device 100 shown in FIG. 6 is such that the inner needle 104 is inserted into the lumen of an outer needle 102 and a needlepoint 141 is most projected from the distal opening of the outer needle 102. In this case, the puncture device 100 has a significant gap between the outer needle 102 and the inner needle 104 (the small diameter portion 142) in a portion L3 where the outer needle 102 covers the small diameter portion 142 of the inner needle 102. The outer needle 102 easily moves on the small diameter portion 142 of the inner needle 104; therefore, when the puncture device 100 is inserted into skin, the outer needle 102 does not follow the inner needle 104, which causes a phenomenon in which only the outer needle 102 is pushed back from the surface of the skin. If the puncture device 100 is forcibly pushed in without change, the outer needle 102 collapses and outwardly rises at a position close to the intermediate portion 143 of the inner needle 104, as shown in FIG. 7. After the outer needle 102 has risen, if the puncture device 100 is further forcibly pushed in, significant puncture resistance is produced to increase the load of the operator and the patient.

Patent Document 1: Japanese Patent Laid-Open No. 2001-112871

DISCLOSURE OF INVENTION

Problem to be Solved by the Invention

It is an object of the present invention to provide a puncture device that does not allow an outer needle to collapse and rise at the time of puncture and has small puncture resistance.

Means for Solving the Problem

Such an object can be achieved by the inventions of items (1) through (13) as below.

(1) A puncture device including: a hollow outer needle; an outer needle hub provided at a proximal end portion of the outer needle and having a lumen portion communicating with the inside of the outer needle; a hollow inner needle inserted into the outer needle and having a sharp needlepoint at a distal end; and an inner needle hub provided at a proximal end portion of the inner needle and having a lumen portion communicating with the inside of the inner needle; wherein the inner needle includes: a small diameter portion located near the needlepoint and having an almost uniform outer diameter; and a larger diameter portion located closer to the proximal end than the small diameter portion and having an outer diameter larger than that of the small diameter portion; and wherein if the inner needle is inserted into the lumen of the outer needle in such a manner that the needlepoint is most projected from the distal opening of the outer needle, the proximal end of the small diameter portion is located in the outer needle and the inner diameter of the outer needle at a portion where the outer needle covers the small diameter portion is smaller than the outer diameter of the larger diameter portion.

(2) The puncture device according to item (1), wherein the inner diameter of the large diameter portion is greater than the inner diameter of the small diameter portion.

(3) The puncture device according to item (1) or (2), wherein the inner needle has an intermediate portion which is located between the small diameter portion and the large diameter portion so as to alleviate the changes of the outer diameters.

(4) The puncture device according to item (3), wherein the intermediate portion is formed as a tapered portion which is progressively increased in outer diameter as the tapered portion goes toward the proximal end.

(5) The puncture device according to any one of items (1) to (4), wherein if the inner needle is inserted into the lumen of the outer needle in such a manner that the needlepoint is most projected from the distal opening of the outer needle, the distal end of the large diameter portion is located inside the outer needle.

(6) The puncture device according to any one of items (1) to (5), wherein the outer needle includes a portion having an almost uniform outer diameter and a tapered portion located closer to the proximal end than the portion and progressively increased in outer diameter as the tapered portion goes toward the proximal end.

(7) The puncture device according to any one of items (1) to (6) wherein the outer needle includes a reduced diameter portion which is located at a distal end portion and is reduced in outer diameter as the reduced diameter portion goes toward the distal end.

(8) The puncture device according to any one of items (1) to (7), wherein the inner diameter of the outer needle is substantially equal to or smaller than the outer diameter of the small diameter portion of the inner needle in a given range from the distal end.

(9) The puncture device according to any one of items (1) to (8), wherein the inner needle hub is formed to enable engagement with the proximal end of the outer needle hub, and if the inner needle is inserted into the lumen of the outer needle in such a manner that the inner hub is engaged with the proximal end of the outer needle hub, the needlepoint is most projected from the distal opening of the outer needle.

(10) The puncture device according to any one of items (1) to (9), wherein the outer needle and the outer needle hub are integrally made of the same material.

(11) The puncture device according to any one of items (1) to (10), wherein if the outer diameter (average) of the small diameter portion of the inner needle is D1 and the outer diameter (average) of the large diameter portion is D2, an outer diameter ratio D1/D2 is from 0.25 to 0.95.

(12) The puncture device according to any one of items (1) to (11), wherein if the inner diameter (average) of the small diameter portion of the inner needle is d1 and the inner diameter (average) of the large diameter portion is d2, an outer diameter ratio d1/d2 is from 0.2 to 0.9.

(13) The puncture device according to any one of items (1) to (12), wherein the puncture device is used for introducing a sheath introducer.

Effect of the Invention

According to the invention, since an outer needle does not collapse or rise at the time of puncture and has small puncture resistance, each of an operator and a patient has a light load.

Figure 1:
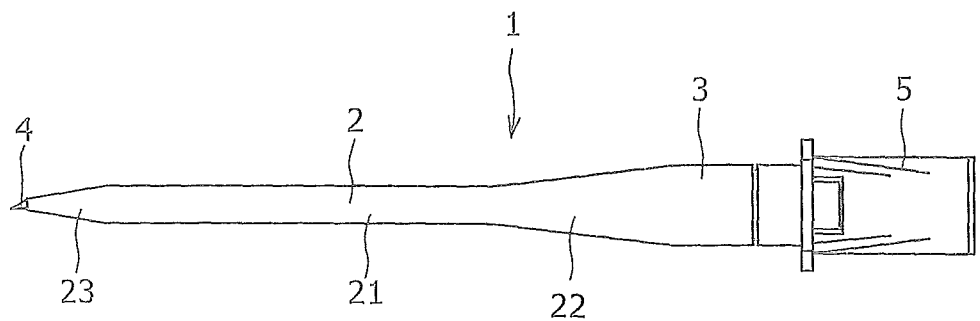
FIG. 1 is a plan view illustrating an embodiment of a puncture device according to the present invention.

DESCRIPTION OF REFERENCE SYMBOLS 1, 100 puncture device
2, 102 outer needle (indwelling needle)
21 uniform outer diameter portion
22 tapered portion
23 reduced diameter portion
24 distal opening
3 outer needle hub
31 inside portion
4, 104 inner needle
41, 141 needlepoint
42, 142 small diameter portion
43, 143 intermediate portion
44, 144 large diameter portion
5 inner needle hub
51 engaging portion (fitting portion)
52 inside portion
53 finger-set portion

BEST MODE FOR CARRYING OUT THE INVENTION

A puncture device of the present invention will hereinafter be described in detail on the basis of a preferred embodiment illustrated in the accompanying drawings.

Figure 2:
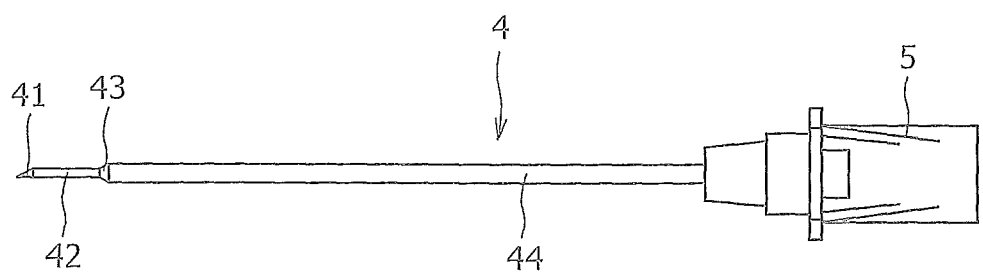
FIG. 2 is a plan view illustrating an inner needle of the puncture device shown in FIG. 1.
Figure 3:
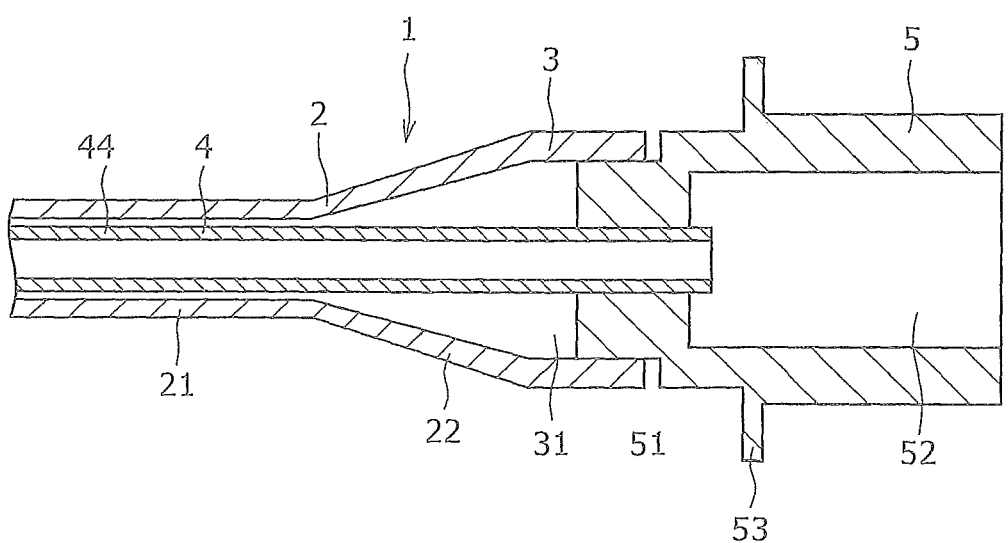
FIG. 3 is an enlarged longitudinal cross-sectional view illustrating the periphery of the proximal end of the puncture device shown in FIG. 1.
Figure 4:
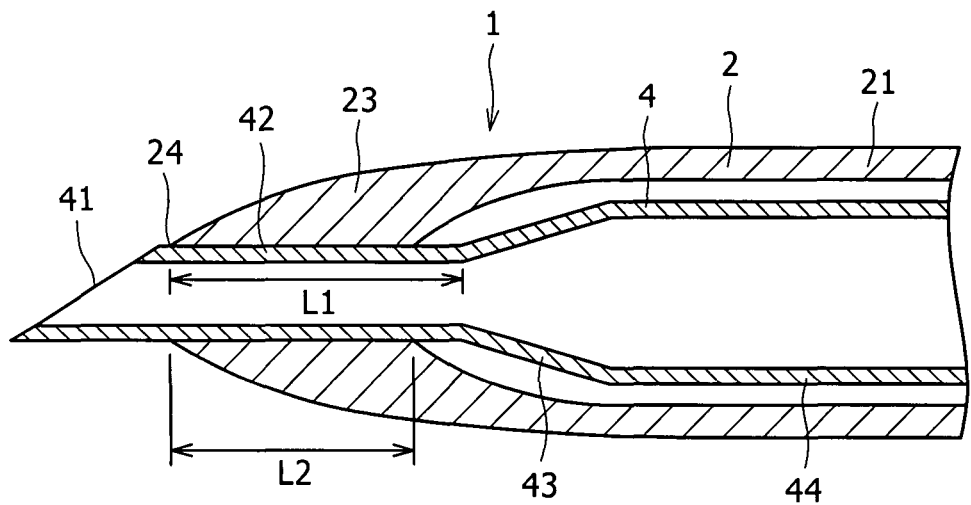
FIG. 4 is an enlarged longitudinal cross-sectional view illustrating the periphery of the distal end of the puncture device shown in FIG. 1.

FIG. 1 is a plan view illustrating an embodiment of the puncture device according to the present invention. FIG. 2 is a plan view illustrating an inner needle of the puncture device shown in FIG. 1. FIG. 3 is an enlarged longitudinal cross-sectional view illustrating the periphery of the proximal end of the puncture device shown in FIG. 1. FIG. 4 is an enlarged longitudinal cross-sectional view illustrating the periphery of the distal end of the puncture device shown in FIG. 1. It is to be note that the right side and the left side in FIGS. 1 to 4 are referred to as "the proximal end" and "the distal end", respectively, in the following description.

Referring to FIGS. 1 through 4, the puncture device (indwelling needle assembly) 1 of the present invention includes a hollow outer needle 2 which is an indwelling needle (introduction needle); and a hollow inner needle 4 which is inserted into the outer needle 2 for use and has a sharp needlepoint 41 at its distal end.

An outer needle hub 3 is formed integrally with the outer needle 2 at the proximal end of the outer needle 2 and made of the same material as the outer needle 2. The outer needle hub 3 has an inside portion (inside space) 31 communicating with the lumen of the outer needle 2. With this configuration, the following advantages can be provided. The number of parts can be reduced and manufacture is facilitated. In addition, the inner surface of a joint between the outer needle hub 3 and the outer needle 2 can be formed to provide a non-stepped smooth surface so that a guide wire can smoothly be inserted into the outer needle 2.

The outer needle 2 includes a uniform outer diameter portion 21 having an almost-uniform outer diameter; and a tapered portion 22 which is progressively increased in outer diameter as it goes toward the proximal end. Further, the outer needle 2 has a reduced diameter portion 23 which is located at its distal end (at the distal side of the uniform outer diameter portion 21) and is (progressively) reduced in outer diameter as it goes toward the distal end. The configuration described above can exhibit the following effects: Puncture for a living body can easily be made without impairing puncture performance (operability). In particular, a puncture wound of a blood vessel can be made small and puncture resistance can be made small so that invasion can be made small at the time of the puncture. Because of the tapered portion 22, the outer needle 2 can ensure sufficient strength (elastic strength) so that it is prevented from being inadvertently curvedly deformed or sharply bent. In addition, the insertion performance of a sheath introducer can be enhanced by the tapered portion 22 widening the puncture portion.

Referring to FIG. 4, the inner needle 4 is inserted into the lumen of the outer needle 2 and its needlepoint 41 is most projected from the distal opening 24 of the outer needle 2 (hereinafter, this state is called "the assembled state"). In this case, the inner diameter of the outer needle 2 at a portion L1 where the outer needle 2 covers the small diameter portion 42 of the inner needle 4 is smaller than the outer diameter of the large diameter portion 44 of the inner needle 4. With the configuration described above, the inner needle 4 is not easily moved on the small diameter portion 42 of the outer needle 2. When the puncture device 1 in the assembled state is inserted into a living body, the outer needle 2 is easily inserted into the living body following the inner needle 4 without only the outer needle 2 being pushed back from the surface of the skin. Thus, the puncture device 1 has advantages of small puncture resistance and of a small load on an operator and a patient. It is to be noted that preferably such a portion L1 has a length ranging from 1 to 30 mm and more preferably from 3 to 10 mm.

The inner diameter of a given range L2 from the distal end (the distal opening 24) of the outer needle 2 is substantially equal to or slightly smaller than the outer diameter of the small diameter portion 42 of the inner needle 4. With this configuration, when the puncture device 1 is brought into the assembled state, the inner circumferential surface of the distal end (the range L2) of the outer needle 2 comes into close contact with the outer circumferential surface of the small diameter portion 42 of the inner needle 4. Therefore, the outer needle 2 more easily follows the inner needle 4. In this case, a difference, in the range L2, between the inner diameter of the outer needle 2 and the outer diameter of the small diameter portion 42 is preferably equal to or less than 0.05 mm, more preferably equal to or less than 0.03 mm. A length L2 preferably ranges from 1 to 30 mm and more preferably from 3 to 10 mm. A ratio of L2 to L1 preferably ranges from 5 to 95%, and more preferably from 20 to 80%.

A taper angle of the tapered portion 22 of the outer needle 2 (an angle of the outer surface relative to the central axis of the outer needle 2) is not particularly restrictive but is preferably from about 5 to about 60°, and more preferably from about 15 to about 25°. Such taper angles allow both the tapered portion 22 to ensure sufficient strength and a living tissue to be widened with small puncture resistance.

The outer diameter and inner diameter of the distal end of the tapered portion 22 are almost equal to the outer diameter and inner diameter, respectively, of the proximal end of the uniform outer diameter portion 21. With this configuration, the outer surface of a boundary portion between the tapered portion 22 and the uniform outer diameter portion 21 becomes a non-stepped smooth surface. Thus, a living tissue such as a skin can be widened while minimizing the puncture resistance of the outer needle 2.

In addition, the inner surface of a boundary portion between the tapered portion 22 and the uniform outer diameter portion 21 becomes a non-stepped smooth surface. Thus, when inserted into the outer needle 2, the guide wire can smoothly be inserted thereinto without being caught.

Preferably, the outer diameter and inner diameter of the proximal end of the tapered portion 22 are substantially equal to the outer diameter and inner diameter, respectively, of the distal end of the outer needle hub 3. With this configuration, the inner surface of a boundary portion between the tapered portion 22 and the outer needle hub 3 becomes a non-stepped smooth surface. Thus, when inserted into the outer needle 2, the guide wire can smoothly be inserted thereinto without being caught.

Since the outer needle 2 is provided with the tapered portion 22 as described above, the tapered portion 22 exhibits a function of widening a living tissue such as skin when the outer needle 2 is inserted into a living body. Consequently, an effect can be provided that insertion resistance encountered when a sheath introducer is inserted is reduced.

The length of the uniform outer diameter portion 21 is not particularly restrictive but is preferably from about 5 to about 100 mm, and more preferably from about 15 to about 60 mm.

The outer diameter (average) of the uniform outer diameter portion 21 is not particularly restrictive but is preferably from about 0.6 to about 2.2 mm, and more preferably from about 1.0 to about 1.8 mm.

The wall thickness of a tube of the uniform outer diameter portion 21 is not particularly restrictive. However, the wall thickness is preferably from about 0.05 to about 0.30 mm, and more preferably from about 0.10 to 0.20 mm, in order not to hinder the outer needle 2 from being reduced in diameter while ensuring sufficient strength.

The length of the taper portion 22 is not restrictive but is preferably from about 3 to about 50 mm, and more preferably from about 5 to about 10 mm.

The maximum outer diameter of the tapered portion (the outer diameter of the proximal end of the tapered portion 22) is not particularly restrictive but is preferably from about 4.0 to about 8.0 mm, and more preferably from about 5.0 to about 6.0 mm.

The wall thickness of the tube of the tapered portion 22 is not particularly restrictive. However, the wall thickness is preferably from about 0.2 to about 2.0 mm, and more preferably from about 0.5 to about 1.0 mm, in order not to hinder the outer needle 2 from being reduced in diameter while ensuring sufficient strength.

The length of the reduced diameter portion 23 is not particularly restrictive and is preferably from about 0.2 to about 30 mm, and more preferably from about 1 to about 10 mm.

The wall thickness of a tube of the most distal end (the neighborhood of the distal opening 24) of the reduced diameter portion 23 is preferably 0.05 mm or less, and more preferably from about 0.01 to about 0.001 mm, in order to reduce a step difference between the outer surface of the inner needle 4 and the distal end of the reduced diameter portion 23.

The constituent material of the outer needle 2 is not particularly restrictive. However, examples of the preferable resin material include: fluorine series resins such as polytetrafluoroethylene (PTFE), ethylene-tetrafluoroethylene copolymer (ETFE), polyethylene propylene-fluoride (FEP), poly perfluoro alkoxy resin (PFA), and polyvinylidene-fluoride resin (PVDF); polyolefin such as polyethylene, polypropylene and polybutylene; polyamide, polyester, polyurethane, polyether-nylon resin. The constituent material of the outer needle 2 may be blended with an X-ray contrast agent such as barium sulfate and barium carbonate to provide a contrast radiography function.

The outer needle 2 described above can be manufactured by e.g., injection molding, extrusion molding, blow molding, heating drawing or other methods.

The outer needle 2 is preferably formed to be longitudinally dividable into a plurality of parts (e.g., two parts). With this configuration, the outer needle 2 can easily be removed with a medical device such as a guide wire indwelled within the body by dividing and removing the outer needle 2 with the medical device inserted therein.

Examples of a configuration of making the outer needle 2 dividable include providing fragile portions (not shown) which are formed of two or more groove portions extending along the longitudinal direction of the outer needle 2.

Referring to FIG. 3, an inner needle hub 5 (housing) formed of an almost cylindrical member is liquid-sealingly joined to the proximal end of the inner needle 4. The inside portion (inside space) 52 of the inner needle hub 5 communicates with the lumen of the inner needle 4. Preferably, the inner needle hub 5 is formed of a transparent or semi-transparent resin to ensure the visibility of the inside portion 52. With this configuration, the needlepoint 41 which has caught the blood vessel can be confirmed by visually observing flashback.

A diameter reduced engaging portion (fitting portion) 51 is formed at the distal end of the inner needle hub 5. In the assembled state, the engaging portion 51 is engaged with (fitted into) the proximal end of the outer needle hub 3 (see FIG. 3). In the assembled state where the outer needle hub 3 is engaged with the inner needle hub 5, the needlepoint 41 of the inner needle 4 is most projected from the distal opening 24 of the outer needle 2.

A flange-like finger-set portion 53 is formed on the distal-side outer circumferential portion of the inner needle hub 5.

An aeration filter (not shown) may be attached to the proximal end of the inner needle hub 5 so as to seal the proximal opening of the inner needle hub 5. The aeration filter passes gas but cannot pass liquid. With this configuration, the blood that has passed through the inner needle 4 and flown in the inside portion 52 of the inner needle hub 5 is prevented from leaking from the proximal opening of the inner needle hub 5. The aeration filter has sufficient aeration property before coming into contact with blood; therefore, a time taken for the flashback can be reduced.

Specific examples of such an aeration filter include sintered porous bodies, hydrophobic nonwoven material and other porous bodies. In this case, a preferable example of the sintered porous bodies includes a sintered material containing polymer material (powder) such as polyethylene and hydrophilic (water-soluble, water-swellable) polymer. The sintered porous body interrupts aeration because of contact with liquid (blood); therefore, air can be prevented from entering from the outside.

The inner needle 4 is made of a metal material such as stainless steel, aluminum, an aluminum alloy, titanium and a titanium alloy. The inner needle 4 is formed with the sharp needlepoint 41 at its distal end. The needlepoint 41 has a pair of blade surfaces inclined at a given angle relative to the axis of the inner needle 4.

As shown in FIGS. 2 and 4, the inner needle 4 includes the small diameter portion 42 and the larger diameter portion 44. The small diameter portion 42 is located near the proximal end of the needlepoint 41 and has an almost uniform outer diameter. The large diameter portion 44 is located closer to the proximal end than the small diameter portion 42 and has an inner diameter and an outer diameter larger than the inner diameter and outer diameter, respectively, of the small diameter portion 42. In addition, the inner needle 4 has the intermediate portion 43 which is located between the small diameter portion 42 and the large diameter portion 44 to alleviate the changes (differences in the outer diameters) of the outer diameters thereof. The intermediate portion 43 is formed of a tapered portion which is progressively increased in outer diameter as it goes toward the proximal end.

With this configuration, puncture for a living body can easily be made without impairing puncture performance (operability). In particular, a puncture wound of a blood vessel can be made small and puncture resistance can be made small so that invasion can be made small at the time of the puncture. A risk of damaging the tissues of a blood vessel, a nerve, a muscle other than the puncture wound can also be reduced. Since the inner diameter of the inner needle is increased from its mid-portion because of the large diameter portion 44, the flow of the blood in the inner needle 4 is promoted to reduce a time taken for the flashback (a time taken for the blood flowing in from the needlepoint 41 to reach the inside of the inner needle hub 5). Thus, it is possible to quickly and reliably recognize that the needlepoint 41 has caught the blood vessel. Because of having the large diameter portion 44, the inner needle 4 ensures sufficient strength (elastic strength) so that it is prevented from being inadvertently curvedly deformed or sharply bent at the time of the puncture or the like.

The large diameter portion 44 may have an almost uniform outer diameter over the full length thereof or may have a tapered portion at, at least, a portion thereof in the longitudinal direction, the tapered portion being progressively increased in outer diameter as it goes toward the proximal end. Alternatively, the large diameter portion may be formed stepwise to have two or more portions different from each other in outer diameter.

As shown in FIG. 4, in the assembled state, the intermediate portion (the tapered portion) 43 of the inner needle 4 is located inside the outer needle 2. That is to say, the distal end of the large diameter portion 44 of the inner needle 4 is located inside the outer needle 4 and also the proximal end of the small diameter portion 42 on the distal side of the large diameter 44 is located inside the outer needle 4.

The length of the needlepoint 41 is not particularly restrictive but is preferably from about 0.5 to about 5.0 mm, and more preferably from about 1.0 to about 3.5 mm.

The length of the small diameter portion 42 is not particularly restrictive but is preferably from about 1 to about 30 mm, and more preferably from about 2 to about 15 mm.

The outer diameter (average) D1 of the small diameter portion 42 is not particularly restrictive but is preferably from about 0.25 to about 1.7 mm and more preferably from about 0.5 to about 1.0 mm.

The inner diameter (average) d1 of the small diameter portion 42 is not particularly restrictive but is preferably from about 0.1 to about 1.5 mm, and more preferably from about 0.3 to about 0.6 mm.

The length of the tapered portion 43 is not particularly restrictive but is preferably from about 0.5 to about 10 mm, and more preferably from about 1 to about 3.5 mm.

The length of the large diameter portion 44 is not particularly restrictive but is preferably from about 10 to about 200 mm and more preferably from about 25 to about 80 mm.

The outer diameter (average) D2 of the large diameter portion 44 is not particularly restrictive but is preferably from about 0.4 to about 2.0 mm and more preferably from about 0.6 to about 1.3 mm.

The inner diameter (average) d2 of the large diameter portion 44 is not particularly restrictive but is preferably from about 0.2 to about 1.8 mm and more preferably from about 0.4 to about 1.1 mm.

Such dimensions described above can provide a satisfactory balance between the strength and puncture performance of the inner needle 4. In particular, the inner needle 4 will not be overcome with the puncture resistance to otherwise bend; therefore, an effect of excellent puncture performance becomes prominent.

The outer diameter ratio D1/D2 is preferably from about 0.25 to about 0.95 and more preferably from about 0.5 to about 0.8. The outer diameter ratio set within such a range allows the inner needle 4 to provide more satisfactory puncture performance while ensuring sufficient strength.

The inner diameter ratio d1/d2 is preferably from about 0.2 to about 0.9 and more preferably from about 0.5 to about 0.8. The inner diameter ratio set within such a range can more reduce a time taken for flashback while allowing the inner needle 4 to ensure sufficient strength and satisfactory puncture performance.

Such an inner needle 4 can be manufactured by a method employing one of or a combination of two or more of plastic processing such as press work, swaging, and drawing, cutting, polishing, laser machining, and etching.

Examples of the constituent material for the inner needle hub 5 include: polyolefin such as polyethylene, polypropylene, ethylene-vinyl acetate copolymer; polyvinyl chloride; polymethylmethacrylate; polycarbonate; polybutadiene; polyamide; polyester such as polyethylene terephthalate, polybutylene terephthalate; acrylic resins; ABS resins; ionomer; polyacetal; polyphenylene sulfide; polyether ether ketone.

A description is next made of how to use the puncture device 1 (of how the puncture device 1 is operated) by way of example.

[1] As shown in FIG. 1, the outer needle 2 and the inner needle 4 are assembled together in advance. In such an assembled state, the needlepoint 41 most projects from the distal opening 24 of the outer needle 2 and the proximal end of the small diameter portion 42 and the distal end of the large diameter portion 44 are accommodated inside the outer needle 2.

[2] The inner needle 4 and outer needle 2 in the assembled state are percutaneously inserted into to a blood vessel (a vein or artery) of a patient.

When the needlepoint 41 of the inner needle 4 is inserted into the blood vessel, blood flows into the inner needle 4 from the opening of the needlepoint 41 due to the inside pressure in the blood vessel (blood pressure), back-flowing toward the proximal end of the inner needle 4, and is introduced into the inside portion 52 of the inner needle hub 5. The flashback can be visualized in the hub 5 having visibility. Thus, it can be recognized that the needlepoint 41 of the inner needle 4 has caught the blood vessel.

[3] When a finger is set on the finger-set portion 53 to fix the inner needle hub 5 and the outer needle hub 3 and the outer needle 2 are advanced toward the distal end in a minute distance, the distal end of the outer needle 2 is inserted into the blood vessel. Thus, the distal end portion of the outer needle 2 catches the blood vessel.

[4] While the outer needle 2 remains indwelled, the inner needle hub 5 is drawn toward the proximal end to withdraw the inner needle 4 from the outer needle 2.

[5] The guide wire (not shown) is inserted into the indwelled outer needle 2 from the proximal opening of the outer needle hub 3. When the distal end of the guide wire reaches inside the blood vessel, the outer needle 2 is withdrawn.

[6] After a sheath introducer in which a dilator is inserted into a sheath is prepared, the sheath introducer is inserted into a living body through the guide wire. When the distal end of the sheath introducer is introduced into the blood vessel, the guide wire and dilator are withdrawn to leave (indwell) the sheath, which catches the blood vessel.

[7] For instance, one of various catheters or a lead wire of a cardiac pacemaker is introduced into the blood vessel via the indwelled sheath implanted.

Incidentally, the application use and usage of the puncture device 1 of the present invention are not limited to the above. For example, after the above process [4], an infusion line is connected to the outer needle hub 3 via a connector. An infusion is fed through the infusion line to the patient for administration.

The puncture device of the present invention has been described thus far with reference to the embodiment illustrated in the drawings. The present invention is not limited to the embodiment described above. The members constituting the puncture device can be replaced with optional constituent members that can exhibit the same respective functions or may be added with respective optional constructions. For instance, an outer needle hub made of a material different from that of the outer needle may be fixedly attached to the proximal end of the outer needle in a liquid-sealed manner.

EXAMPLES

A description is next made of a specific example of the puncture device of the present invention.

Figure 5:
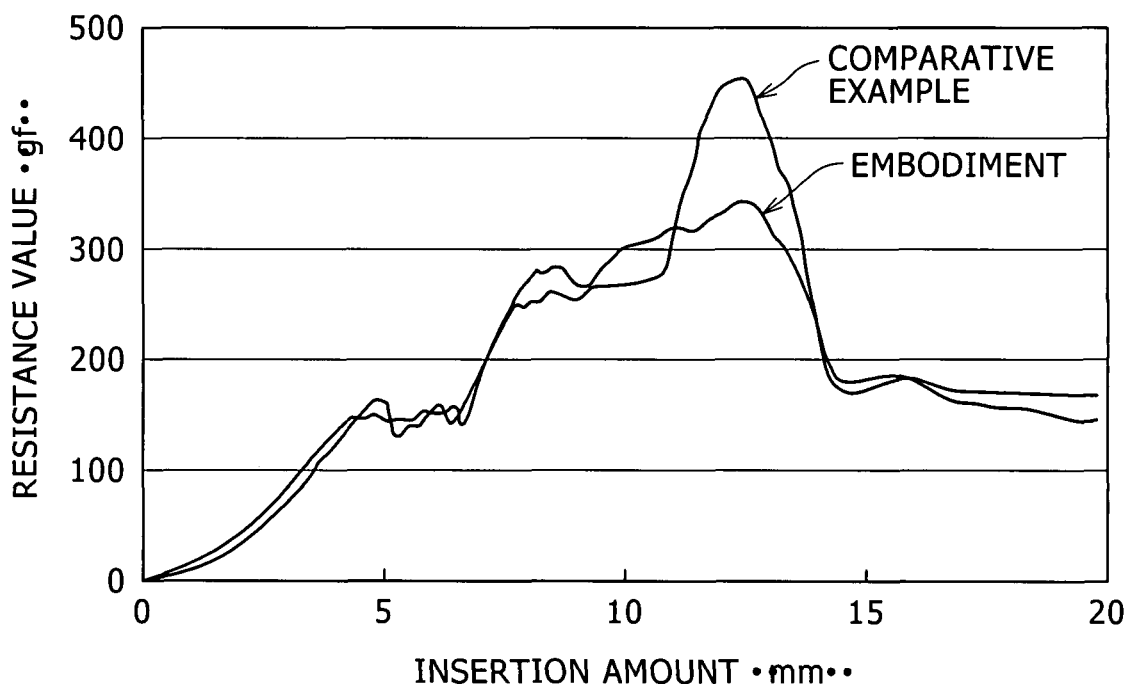
FIG. 5 is a graph illustrating the relationship between insertion amounts and resistance values in the embodiment and a comparative example.

The puncture device shown in FIGS. 1 to 4 was manufactured. The dimensions of the puncture device are as follows:

The outer diameter of the small diameter portion 42 of the inner needle 4: 0.90 mm The length of the small diameter portion 42 of the inner needle 4: 6 mm The length of the intermediate portion 43 of the inner needle 4: 3 mm The outer diameter of the large diameter portion 44 of the inner needle 4: 1.25 mm The length (L2) of a portion of the outer needle 2 in close contact with the small diameter portion 44 of the inner needle 4: 5 mm The inner diameter of the outer needle 2 at a portion corresponding to the boundary portion between the small diameter portion 42 and intermediate portion 43 of the inner needle 4: 0.98 mm The inner diameter of the outer needle 2 at a portion corresponding to the large diameter portion of the inner needle 4: 1.30 mm Next, the puncture device was inserted at 20 mm deep into cattle hide with a thickness of 1 mm at an angle of 45° and the resistance values relative to the respective puncture distances (insertion amounts) were determined. FIG. 5 shows the results.

FIG. 5 shows that the maximum resistance value is 343 gf. Collapse or rise of the outer needle was not particularly found after 20-mm-deep insertion.

Comparative Example 5

Figure 6:
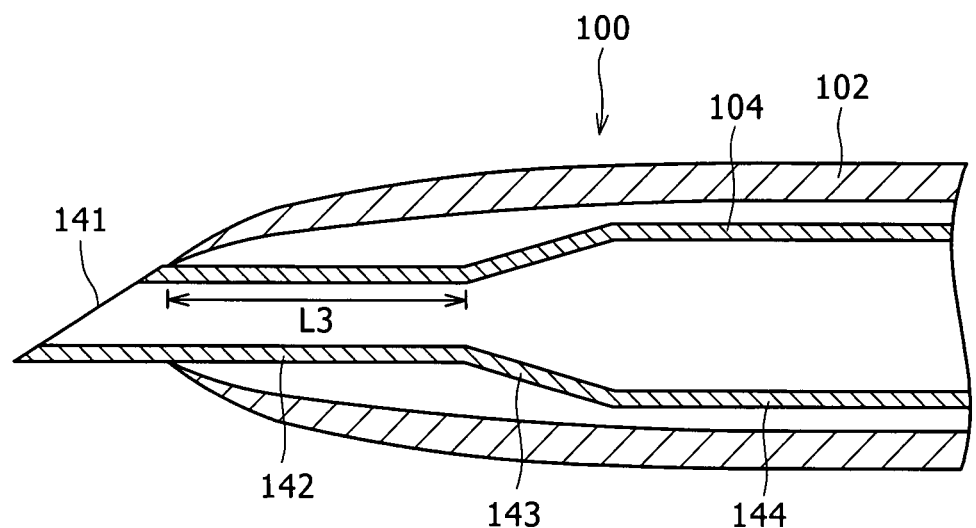
FIG. 6 is a plan view illustrating a conventional puncture device.
Figure 7:
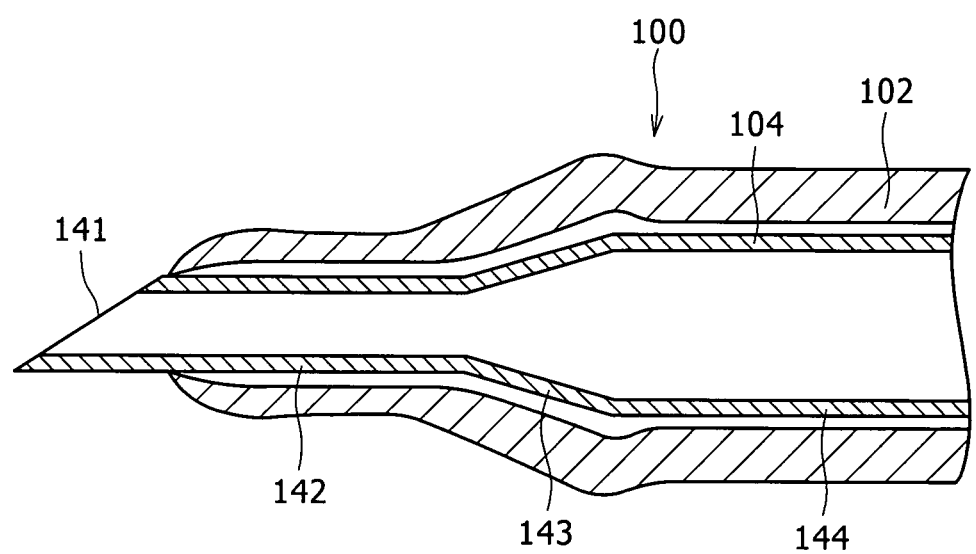
FIG. 7 is a plan view illustrating the puncture device shown in FIG. 6 which is inserted.

The puncture device of FIG. 6 was manufactured. The dimensions of the puncture device are as follows:

The outer diameter of the small diameter portion 142 of the inner needle 104: 0.90 mm The length of the small diameter portion 142 of the inner needle 104: 6 mm The length of the intermediate portion 143 of the inner needle 104: 3 mm The outer diameter of the large diameter portion 144 of the inner needle 104: 1.25 mm The length of a portion of the outer needle 102 in close contact with the small diameter portion 144 of the inner needle 104: 1 mm The inner diameter of the outer needle 102 at a portion corresponding to the boundary portion between the small diameter portion 142 and intermediate portion 143 of the inner needle 104: 1.30 mm The inner diameter of the outer needle 102 at a portion corresponding to the large diameter portion of the inner needle 104: 1.30 mm Next, the resistance values relative to the respective puncture distances (insertion amounts) were determined in the same manner as those of the embodiment. FIG. 5 shows the results.

FIG. 5 shows that the maximum resistance value is 454 gf, which is about 1.3 times greater than that of the embodiment. Rise of the outer needle was found after 20-mm-deep insertion.

The invention claimed is:

1. A puncture device comprising:
a hollow outer needle having a lumen communicating with a distal opening of the outer needle;
an outer needle hub provided at a proximal end portion of the outer needle and having a lumen portion communicating with the lumen of the outer needle;
a hollow inner needle positioned in the lumen of the outer needle and configured to be completely removable from the lumen of the outer needle, the hollow inner needle having a lumen and a sharp needlepoint at a distal end, the inner needle possessing a distal opening communicating with the lumen of the inner needle;
an inner needle hub provided at a proximal end portion of the inner needle and having a lumen portion communicating with the lumen of the inner needle;
the outer needle and the inner needle, and the inner needle hub and the outer needle hub, being configured so that a proximal end of the outer needle hub is contactable by the inner needle hub;
wherein the inner needle includes:
a smaller diameter portion located near the needlepoint and having an almost uniform outer diameter, the almost uniform outer diameter of the smaller diameter portion terminating at a proximal-most end;
an intermediate portion possessing a distal-most end directly connected to the proximal-most end of the smaller diameter portion, the intermediate portion also possessing a proximal-most end, the entirety of the intermediate portion being a non-stepped smooth tapered portion which is progressively increased in outer diameter towards the proximal-most end of the intermediate portion to reduce insertion resistance encountered when the intermediate portion of the puncture device is inserted into an insertion site;
a larger diameter portion located closer to a proximal end of the inner needle than the smaller diameter portion and having an outer diameter larger than that of the smaller diameter portion, the larger diameter portion possessing a distal-most end directly connected to the proximal-most end of the intermediate portion;
the proximal-most end of the smaller diameter portion possessing an outer diameter the same as the outer diameter of the distal-most end of the intermediate portion so that a smooth non-stepped transition exists between the smaller diameter portion and the intermediate portion;
the sharp needlepoint of the inner needle projecting distally beyond a distal-most end of the outer needle when the proximal end of the outer needle hub is contacted by the inner needle hub so that during puncture of a living body with the puncture device, the living body is first punctured by the sharp needlepoint of the inner needle;
the inner needle being positioned in the lumen of the outer needle in such a manner that with the needlepoint projecting distally beyond the distal opening of the outer needle, the proximal end of the smaller diameter portion is located in and covered by the outer needle, and the inner diameter of the outer needle at a portion where the outer needle covers the smaller diameter portion is smaller than the outer diameter of the larger diameter portion; and
the inner diameter of the outer needle at the portion where the outer needle covers the smaller diameter portion is smaller than the outer diameter of the smaller diameter portion of the inner needle in a given range from a distal end of the outer needle.

2. The puncture device according to claim 1, wherein the inner diameter of the larger diameter portion is greater than the inner diameter of the smaller diameter portion.

3. The puncture device according to claim 2, wherein the outer needle includes a portion having an almost uniform outer diameter and a tapered portion located closer to the proximal end than the portion and progressively increased in outer diameter as the tapered portion goes toward the proximal end.

4. The puncture device according to claim 2, wherein the outer needle includes a reduced diameter portion which is located at a distal end portion and is reduced in outer diameter as the reduced diameter portion goes toward the distal end.

5. The puncture device according to claim 2, wherein the outer needle and the outer needle hub are integrally made of the same material.

6. The puncture device according to claim 2, wherein an outer diameter ratio D1/D2 is from 0.25 to 0.95, where D1 represents the outer diameter (average) of the smaller diameter portion of the inner needle and D2 represents the outer diameter (average) of the larger diameter portion.

7. The puncture device according to claim 2, wherein an inner diameter ratio d1/d2 is from 0.2 to 0.9, where d1 is the inner diameter (average) of the smaller diameter portion of the inner needle and d2 is the inner diameter (average) of the larger diameter portion.

8. The puncture device according to claim 1, wherein with the inner needle positioned in the lumen of the outer needle in such a manner that the needlepoint projects distally from the distal opening of the outer needle, the distal end of the larger diameter portion is located inside the outer needle.

9. The puncture device according to claim 1, wherein the outer needle includes a portion having an almost uniform outer diameter and a tapered portion located closer to the proximal end than the portion and progressively increased in outer diameter as the tapered portion goes toward the proximal end.

10. The puncture device according to claim 1, wherein the outer needle includes a reduced diameter portion which is located at a distal end portion and is reduced in outer diameter as the reduced diameter portion goes toward the distal end.

11. The puncture device according to claim 1, wherein the outer needle and the outer needle hub are integrally made of the same material.

12. The puncture device according to claim 1, wherein if the outer diameter (average) of the smaller diameter portion of the inner needle is D1 and the outer diameter (average) of the larger diameter portion is D2, an outer diameter ratio D1/D2 is from 0.25 to 0.95.

13. The puncture device according to claim 1, wherein if the inner diameter (average) of the smaller diameter portion of the inner needle is d1 and the inner diameter (average) of the larger diameter portion is d2, an inner diameter ratio d1/d2 is from 0.2 to 0.9.

14. The puncture device according to claim 1, wherein the puncture device is used for introducing a sheath introducer.

15. The puncture device according to claim 1, wherein an inner surface of a distal-most end portion of the outer needle contacts an outer surface of a distal-most end portion of the inner needle, wherein the distal-most end portion of the outer needle whose inner surface is in contact with the outer surface of the distal-most end portion of the inner needle terminates at a proximal end, the inner surface of a first portion of the outer needle being spaced from the outer surface of the inner needle so that a space exists between the inner surface of the first portion of the outer needle and the outer surface of the inner needle, the inner surface of a second portion of the outer needle being spaced from the outer surface of the inner needle so that a space exists between the inner surface of the second portion of the outer needle and the outer surface of the inner needle, the first portion of the outer needle extending from the proximal end of the distal-most end portion of the outer needle to a proximal end of the first portion, and the second portion extending from the proximal end of the first portion to a proximal end of the second portion, a radial dimension of the space between the inner surface of the outer needle and the outer surface of the inner needle in at least a part of the first portion being larger than a radial dimension of the space between the inner surface of the outer needle and the outer surface of the inner needle in at least a part of the second portion.

16. The puncture device according to claim 1, wherein the sharp needlepoint is beveled so that a distal-most tip of the needlepoint is spaced radially outwardly of a central axis of the inner needle.

17. The puncture device according to claim 1, wherein an inner diameter of the larger diameter portion of the inner needle is larger than the outer diameter of the smaller diameter portion of the inner needle.

18. A puncture device comprising:
a hollow outer needle having a lumen communicating with a distal opening of the outer needle, the outer needle comprising a tapering proximal end portion possessing tapering inner and outer surfaces increasing in size toward a proximal-most end of the outer needle, the tapering inner surface terminating at the proximal-most end of the outer needle;
an outer needle hub extending proximally from the proximal-most end of the tapering proximal end portion of the outer needle and having a lumen portion communicating with the lumen of the outer needle, the outer needle hub possessing a distal-most end connected to the proximal-most end of the tapering proximal end portion of the outer needle, the outer needle hub possessing an inner surface;
a hollow inner needle positioned in the lumen of the outer needle, the hollow inner needle having a lumen and a sharp needlepoint at a distal end of the hollow inner needle, the inner needle possessing a distal opening communicating with the lumen of the inner needle;
an inner needle hub at a proximal end portion of the inner needle and having a lumen portion communicating with the lumen of the inner needle, the inner needle hub possessing a distal-most end;
wherein the inner needle includes:
a smaller diameter portion located near the needlepoint and having an almost uniform outer diameter extending from a proximal-most end of the smaller diameter portion to a distal-most end of the smaller diameter portion;
an intermediate portion having a proximal-most end and a distal-most end at which the intermediate portion terminates, the distal-most end of the intermediate portion being directly connected to the proximal-most end of the smaller diameter portion, the entirety of the intermediate portion being a non-stepped smooth tapered portion which is progressively increased in outer diameter towards the proximal-most end of the intermediate portion to reduce insertion resistance encountered when the intermediate portion of the puncture device is inserted into an insertion site;
a larger diameter portion located closer to a proximal end of the inner needle than the smaller diameter portion and having an outer diameter larger than that of the smaller diameter portion, the larger diameter portion having a proximal-most end and a distal-most end at which the larger diameter portion terminates, the distal-most end of the larger diameter portion being directly connected to the proximal-most end of the intermediate portion;
the proximal-most end of the smaller diameter portion and the distal-most end of the intermediate portion being configured so that a smooth non-stepped transition exists between the smaller diameter portion and the intermediate portion;
the inner needle and the outer needle being configured so that the sharp needlepoint of the inner needle is positionable distally beyond a distal-most end of the outer needle;
the inner needle being positioned in the lumen of the outer needle in such a manner that with the needlepoint projecting distally beyond the distal opening of the outer needle, the proximal end of the smaller diameter portion is located in and covered by the outer needle, and the inner diameter of the outer needle at a portion where the outer needle covers the smaller diameter portion is smaller than the outer diameter of the larger diameter portion;
the puncture device being devoid of structure which moves together with the inner needle and which contacts the inner surface of the outer needle hub distal of the distal-most end of the inner needle hub; and
the inner diameter of the outer needle at the portion where the outer needle covers the smaller diameter portion is smaller than the outer diameter of the smaller diameter portion of the inner needle in a given range from a distal end of the outer needle.

19. The puncture device according to claim 18, wherein an inner surface of a distal-most end portion of the outer needle contacts an outer surface of a distal-most end portion of the inner needle, wherein the distal-most end portion of the outer needle whose inner surface is in contact with the outer surface of the distal-most end portion of the inner needle terminates at a proximal end, the inner surface of a first portion of the outer needle being spaced from the outer surface of the inner needle so that a space exists between the inner surface of the first portion of the outer needle and the outer surface of the inner needle, the inner surface of a second portion of the outer needle being spaced from the outer surface of the inner needle so that a space exists between the inner surface of the second portion of the outer needle and the outer surface of the inner needle, the first portion of the outer needle extending from the proximal end of the distal-most end portion of the outer needle to a proximal end of the first portion, and the second portion extending from the proximal end of the first portion to a proximal end of the second portion, a radial dimension of the space between the inner surface of the outer needle and the outer surface of the inner needle in at least a part of the first portion being larger than a radial dimension of the space between the inner surface of the outer needle and the outer surface of the inner needle in at least a part of the second portion.

20. The puncture device according to claim 18, wherein the sharp needlepoint is beveled so that a distal-most tip of the needlepoint is spaced radially outwardly of a central axis of the inner needle.

21. The puncture device according to claim 18, wherein an inner diameter of the larger diameter portion of the inner needle is larger than the outer diameter of the smaller diameter portion of the inner needle.

22. A method of using a puncture device comprising:

percutaneously inserting an assembled inner needle and outer needle of a puncture device in a blood vessel, the puncture device comprising:

the outer needle being hollow and having a lumen communicating with a distal opening of the outer needle; an outer needle hub at a proximal end portion of the outer needle and having a lumen portion communicating with the lumen of the outer needle; the inner needle being hollow and positioned in the lumen of the outer needle, the hollow inner needle having a lumen and a sharp needlepoint at a distal end of the hollow inner needle, the inner needle possessing a distal opening communicating with the lumen of the inner needle; an inner needle hub at a proximal end portion of the inner needle and having a lumen portion communicating with the lumen of the inner needle;

the inner needle including a smaller diameter portion located near the needlepoint and having an almost uniform outer diameter which extends from a distal-most end of the smaller diameter portion to a proximal-most end of the smaller diameter portion; the inner needle hub also including a larger diameter portion located closer to a proximal end of the inner needle than the smaller diameter portion and having an outer diameter larger than that of the smaller diameter portion; the larger diameter portion terminating at a distal-most end and a proximal-most end; the inner needle also including an intermediate portion terminating at a distal-most end and a proximal-most end, the distal-most end of the intermediate portion being directly connected to the proximal-most end of the smaller diameter portion, the proximal-most end of the intermediate portion being directly connected to the distal-most end of the larger diameter portion, the entirety of the intermediate portion being a non-stepped smooth tapered portion which is progressively increased in outer diameter toward the proximal-most end of the intermediate portion to reduce insertion resistance encountered when the intermediate portion of the puncture device is inserted; the proximal-most end of the smaller diameter portion and the distal-most end of the intermediate portion being configured so that a smooth non-stepped transition exists between the smaller diameter portion and the intermediate portion; the inner needle and the outer needle being configured so that the sharp needlepoint of the inner needle is positionable distally beyond a distal-most end of the outer needle; and the inner diameter of the outer needle at the portion where the outer needle covers the smaller diameter portion is smaller than the outer diameter of the smaller diameter portion of the inner needle in a given range from a distal end of the outer needle;

the inner needle being positioned in the lumen of the outer needle in such a manner that with the needlepoint projecting distally beyond the distal opening of the outer needle, the proximal end of the smaller diameter portion is located in and covered by the outer needle, and the inner diameter of the outer needle at a portion where the outer needle covers the smaller diameter portion is smaller than the outer diameter of the larger diameter portion;

the assembled inner needle and outer needle being percutaneously inserted in the blood vessel so that blood in the blood vessel flows into the inner needle hub by way of the lumen in the inner needle while the inner and outer needles are indwelled in the blood vessel; and completely withdrawing the inner needle from within the outer needle while the outer needle remains indwelled in the blood vessel.

23. The method according to claim 22, further comprising inserting a medical instrument into the lumen of the outer needle by way of the outer needle hub after the inner needle is completely withdrawn from within the outer needle.

24. The method according to claim 22, wherein the percutaneous insertion of the assembled inner needle and outer needle of the puncture device in the blood vessel comprises percutaneously inserting the assembled inner needle and outer needle of the puncture device in a blood vessel of a human body so that at least a distal part of the larger diameter portion of the inner needle is positioned in the human body.

25. A puncture device comprising:

a hollow outer needle having a lumen communicating with a distal opening of the outer needle;

an outer needle hub provided at a proximal end portion of the outer needle and having a lumen portion communicating with the lumen of the outer needle;

a hollow inner needle positioned in the lumen of the outer needle, the hollow inner needle having a lumen and a sharp needlepoint at a distal end, the inner needle possessing a distal opening communicating with the lumen of the inner needle, the inner needle being positionable in the outer needle such that the sharp needlepoint at the distal end of the inner needle projects distally beyond the distal opening of the outer needle;

an inner needle hub provided at a proximal end portion of the inner needle and having a lumen portion communicating with the lumen of the inner needle;

wherein the inner needle includes:

a smaller diameter portion located near the needlepoint and having an almost uniform outer diameter;

a larger diameter portion located closer to a proximal end of the inner needle than the smaller diameter portion and having an outer diameter larger than that of the smaller diameter portion;

the inner needle being positioned in the lumen of the outer needle so that with the needlepoint projecting distally beyond the distal opening of the outer needle, a distal portion of the outer needle surrounds the smaller diameter portion of the inner needle, and the inner diameter of the distal portion of the outer needle is smaller than the outer diameter of the larger diameter portion of the inner needle; and the inner diameter of the distal portion of the outer needle is smaller than the outer diameter of the smaller diameter portion of the inner needle over a length extending from a distal end of the outer needle.

26. The puncture device according to claim 25, wherein an inner diameter of the larger diameter portion of the inner needle is larger than the outer diameter of the smaller diameter portion of the inner needle.

27. The puncture device according to claim 25, wherein the smaller diameter portion of the inner needle possesses a proximal-most end so that the smaller diameter portion extends from a distal-most end of the inner needle to the proximal-most end of the smaller diameter portion; the inner needle and the outer needle being configured so that the sharp needlepoint of the inner needle projects distally beyond the distal-most end of the outer needle when the outer needle hub contacts a proximal end of the inner needle hub so that during puncture of a living body with the puncture device, the living body is first punctured by the sharp needlepoint of the inner needle.

28. The puncture device according to claim 25, wherein the inner needle includes an intermediate tapered portion between the smaller diameter portion and the larger diameter portion.

* * * * *